United States Patent [19]
White et al.

[11] Patent Number: 5,188,120
[45] Date of Patent: Feb. 23, 1993

[54] MEASURING DEVICE FOR MEASURING THE DIAMETER OF THE HYMENAL ORIFICE

[75] Inventors: Susanne T. White, New Orleans, La.; Pauline R. Lyna, Cary; W. Joy Fay, Lillington, both of N.C.

[73] Assignee: Child Sexual Abuse Team, Wake AHEC, Raleigh, N.C.

[21] Appl. No.: 852,108

[22] Filed: Mar. 16, 1992

[51] Int. Cl.⁵ ............................................. A61B 5/03
[52] U.S. Cl. ....................................... 128/778; 33/512
[58] Field of Search ...................... 128/774, 775, 778; 606/234–236; 33/511, 512, 555.1

[56] References Cited

U.S. PATENT DOCUMENTS

| | | | |
|---|---|---|---|
| 3,224,412 | 12/1965 | Fuentes | 33/511 |
| 4,211,241 | 7/1980 | Kaster et al. | 33/512 |
| 4,226,025 | 10/1980 | Wheeler | 128/774 |
| 5,018,531 | 5/1991 | Hartman | 128/774 |
| 5,033,864 | 7/1991 | Lasecki et al. | 606/234 |
| 5,034,009 | 7/1991 | Mouchel | 128/778 |
| 5,042,161 | 8/1991 | Hodge | 128/774 |

FOREIGN PATENT DOCUMENTS

| | | | |
|---|---|---|---|
| 2837438 | 3/1980 | Fed. Rep. of Germany | 606/235 |
| 1454435 | 1/1989 | U.S.S.R. | 128/774 |

*Primary Examiner*—Max Hindenburg
*Attorney, Agent, or Firm*—Rhodes, Coats & Bennett

[57] ABSTRACT

A measuring device is disclosed for accurately measuring the hymenal orifice diameter of female children being evaluated for suspected sexual abuse. The measuring device includes a main body member comprised of a handle portion and an extended portion. Attached to one end of the extended portion is a transparent measuring member. The transparent measuring member is circular and has demarcations inscribed thereon for making measurements. A smiling face is also inscribed on the measuring member to alleviate the anxiety of the female child being examined. The measuring device is used by gripping the handle portion and positioning the measuring member over the hymenal orifice. When the measuring member is positioned over the hymenal orifice, each end of the hymenal orifice can be visualized through the transparent measuring member and the demarcations can be used to determine its diameter.

10 Claims, 1 Drawing Sheet

MEASURING DEVICE FOR MEASURING THE DIAMETER OF THE HYMENAL ORIFICE

FIELD OF INVENTION

The present invention relates generally to medical measuring devices, and more particularly to medical measuring devices for measuring the diameter of the hymenal orifice in female children.

BACKGROUND OF THE INVENTION

Healthcare professionals across the country involved in the evaluation of children suspected of sexual abuse have expressed the need for a device to accurately measure the diameter of the hymenal orifice. These professionals have expressed dissatisfaction with the prior art devices and methods that are now used to measure the hymenal orifice diameter, which make it difficult for doctors to obtain accurate measurements. In addition, these prior art devices often result in unnecessary anxiety to the child patient.

One prior art device for making measurements is by positioning a paper tape measure adjacent to the hymenal orifice. Due to the flexibility of the paper and the inability to effectively position the tape measure, doctors have difficulty in making accurate measurements of the hymenal orifice diameter using this technique. Another method that has been tried is to attach a tape measure to a tongue blade and then place the device in front of the hymenal orifice. A user of this type of measuring device is still unable to easily obtain an accurate measurement because portions of the hymenal orifice may be blocked from the doctor's view.

SUMMARY AND OBJECTS OF THE INVENTION

The present invention is a measuring device for making accurate measurements of the hymenal orifice diameter while helping to alleviate the anxiety of the child undergoing the examination. The measuring device includes a main body member and a measuring member that is attached to one end of the main body member. The measuring member has a circular shape and is transparent. Demarcations are outlined on the transparency for making measurements of the hymenal orifice diameter. In addition, a smiling face is outline on the measuring member to alleviate a child's anxiety during the examination process. The main body member serves as a handle and extension to aid in properly positioning the measuring member at the hymenal orifice during the examination. The transparency of the measuring member enables the user examining the child to visualize each end of the hymenal orifice while the measurement is being taken. The ability to see each end of the hymenal orifice through the measuring member permits the user to more precisely reference the demarcations with each end of the hymenal orifice, and thus, make a more accurate measurement.

Accordingly, it is an object of the present invention to provide a measuring device that can be effectively positioned at the hymenal orifice such that an accurate measurement can be made of the hymenal orifice.

Another object of the present invention is to provide a measuring device that is transparent to allow each end of the hymenal orifice to be visualized during the measurement of the diameter of the hymenal orifice.

Another object of the present invention is to provide a measuring member which has sufficient rigidity to prevent bending of the measuring member during the measurement of the hymenal orifice.

Another object of the present invention is to provide a handle that allows easy maneuverability of the measuring member by the examiner.

Another object of the present invention is to provide a handle to the measuring member that enables the user to position the measuring member at the hymenal orifice and to view the measuring member without the user's hand blocking the user's line of sight to the measuring member.

Another object of the present invention is to lessen the anxiety of the child during the examination procedure.

Other objects and advantages of the present invention will become apparent and obvious from a study of the following description and the accompanying drawings which are merely illustrative of such invention.

DETAILED DESCRIPTION OF THE INVENTION

Figure 1:
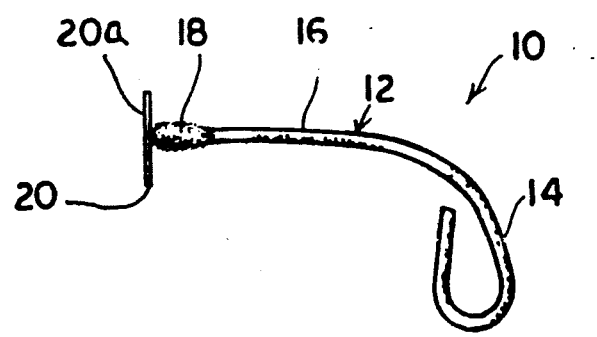
FIG. 1 is a side elevation view of the measuring device.
Figure 2:
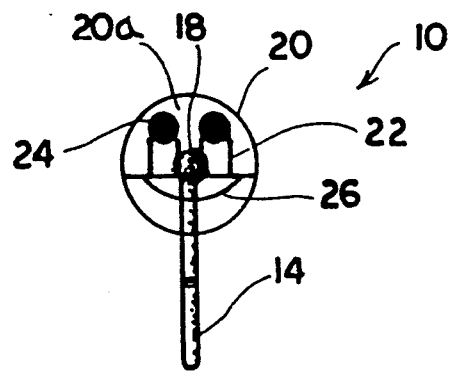
FIG. 2 is a front elevation view of the measuring device.

Referring to the drawings, the measuring device of the present invention is indicated generally by the numeral 10. Measuring device 10 includes a main body member indicated generally by the numeral 12. In the preferred embodiment of the invention, the main body member is formed from a calgi-swab. Main body member 12 includes a handle portion 14 and an extended portion 16. Attached to the end of the extended portion opposite handle portion 14 is a swab 18.

A measuring member 20 is attached to the swab 18 at the end of the main body member 12. Measuring member 20 is made of a transparent plastic and has a circular shape. Inscribed on a face section 20a of the measuring member 20 are demarcations 22 that are two millimeters apart and are formed by spaced solid lines. Face section 20a of the measuring member 20 portrays a smiling face with a pair of solid black dots 24 that form the eyes of the smiling face and a solid curved line 26 that forms the mouth of the smiling face.

A doctor or other examiner uses the measuring device 10 as follows. The doctor grips the handle portion 14 that has the attached measuring member 20 at the opposite end of the main body member 12. The measuring member 20 is extended from the doctor's hand by the extended portion 16 such that the doctor's hand does not hinder the positioning of the measuring member 20 or block the view of the hymenal orifice.

Prior to positioning the measuring device 10 at the hymenal orifice, the doctor can explain to the child the manner in which the child will be examined. As a part of this explanation and in order to ease the anxiety of the child, the doctor can show the measuring device 10 to the child. Because the measuring member 20 of the measuring device 10 has a smiling face inscribed on face section 20a, the anxiety of the child may be lessened and the stress of the examination lessened.

After showing the child the measuring device 10, the doctor with the handle portion 14 gripped in her hand can easily position the measuring member 20 adjacent to the hymenal orifice. Because the handle portion 14 is angled downwardly from the extension member the doctor's hand gripping the measuring device 10 does not interfere with the doctor's view of the hymenal orifice and adjacent measuring member. The shape of the main body member 12, and in particular, the angle that handle 14 makes with extended portion 16 provides the examiner with an unobstructed view of the measuring member 20 and underlying hymenal orifice.

The transparency of the measuring member 20 allows the examiner to view each end of the hymenal orifice while the measuring member 20 is adjacent thereto. Likewise, the relative rigidity of the measuring member 20 prevents the measuring member 20 from bending during examination of the child. Accordingly, the demarcations 22 on face section 20a are not misaligned during examination due to bending of the measuring member, and a correct reading from the measuring member 20 can be made by the examiner.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A measuring device for measuring the hymenal orifice diameter of a female patient, comprising:
   a) a main body member comprised of a handle portion and an extended portion having a first end and a second end, wherein the first end of the extended portion attaches to the handle portion, and wherein the extended portion extends at an angle from the handle portion;
   b) a transparent measuring member attached to the second end of the extended portion, said measuring member including a face section, and wherein the face section is positionable adjacent to the hymenal orifice during measurement of the hymenal orifice diameter; and
   c) a plurality of demarcations associated with the face section of the measuring member and spaced at predetermined intervals for measuring the diameter of the hymenal orification when the measuring members disposed adjacent to the hymenal orifice.

2. The measuring device of claim 1 wherein the measuring member is sufficiently rigid to prevent bending of the measuring member during the measurement process.

3. The measuring device of claim 1 wherein the measuring member is circular.

4. The measuring device of claim 1 wherein the measuring member includes a pictorial design inscribed thereon for alleviating the anxiety of a child undergoing the examination.

5. The measuring device of claim 4 wherein the pictorial design inscribed on the measuring member is a smiling face.

6. A measuring device for measuring the hymenal orifice diameter of a female patient, comprising:
   a) a main body member having an extended portion, the extended portion including an end;
   b) a measuring member attached to the end of the extended portion and the measuring member including a face section that is positionable adjacent to the hymenal orifice during measurement of the hymenal orifice diameter; and
   c) a plurality of demarcations associated with the face section of the measuring member and spaced at predetermined intervals for determining the diameter of the hymenal orifice when the measuring member is positioned adjacent to the hymenal orifice.

7. The measuring device of claim 6 wherein the measuring member is of sufficient rigidity to prevent bending of the measuring member during the measurement process.

8. The measuring device of claim 6 wherein the measuring member is circular.

9. The measuring device of claim 6 wherein the measuring member includes a pictorial design inscribed thereon for alleviating the anxiety of a child undergoing the examination.

10. The measuring device of claim 9 wherein the pictorial design inscribed on the measuring member is a smiling face.

* * * * *